United States Patent [19]

Zikria et al.

[11] Patent Number: 5,685,302

[45] Date of Patent: Nov. 11, 1997

[54] METHOD FOR DETERMINING PLASMA VOLUME, DETERMINATION OF BLOOD VOLUME THEREBY, AND APPARATUS THEREFORE

[75] Inventors: Bashir A. Zikria, Norwood, N.J.; Alain N. Nicoletta, Newark, Del.

[73] Assignee: The Trustees of Columbia University in the City of New York, New York, N.Y.

[21] Appl. No.: 344,335

[22] Filed: Nov. 22, 1994

[51] Int. Cl.⁶ .................................................. A61B 5/00
[52] U.S. Cl. ........................ 128/637; 128/630; 128/638; 128/654; 128/659
[58] Field of Search ............................ 128/630, 637, 128/638, 654, 659, 691, 668, 898; 600/4, 5

[56] References Cited

U.S. PATENT DOCUMENTS 4,994,444  2/1991  Zikria .
5,024,231  6/1991  Fledschuh et al. .................... 128/654

OTHER PUBLICATIONS

Fleck, A., et al., Increased Vascular Permeability: A Major Cause of Hypoalbuminaemia In Disease and Injury. The Lancet (1985).
1(8432): 781–784 (Exhibit C).
Gosling, P., et al. Generalized Vascular Permeability and Pulmonary Function in Patients Following Serious Trauma. The Journal of Trauma (1994) 36(4): 477–481 (Exhibit D).
Shippy, C. R., et al., Reliability of Clinical Monitoring to Assess Blood Volume in Critically Ill Patients. Critical Care Medicine (1984) 12(2): 107–112 (Exhibit E).

Shoemaker, W.C., Pathophysiology and Fluid Management of Postoperative and Post–Traumatic ARDS. Assessment of Blood Volume Deficit.

Shoemaker, W. C., et al. eds. Textbook of Critical Care. Philadelphia: Saunders (1989), p. 626 (Exhibit F).

Valeri, C.R., et al. Limitations of Measuring Blood Volume With Iodinated I 125 Serum Albumin. Archives of Internal Medicine (1973) 132(4):534–538 (Exhibit G).

*Primary Examiner*—Robert L. Nasser
*Attorney, Agent, or Firm*—John P. White

[57] ABSTRACT

The subject invention provides a method for determining in a subject the volume of plasma in the subject's circulation which comprises introducing into the subject's circulation a predetermined amount of a pharmaceutically-acceptable solution comprising a predetermined quantity of biodegradable, nontoxic macromolecules, which macromolecules are sufficiently larger than endothelial junctions in the subject's capillaries so that they are incapable of permeating the subject's capillaries, and each of which macromolecules is labeled with a detectable marker; obtaining a sample of plasma from the subject; determining the concentration of macromolecules in the sample; and calculating the volume of liquid which would dilute the sample to the concentration so determined. The subject invention also provides a method for determining in a subject the volume of blood in the subject's circulation which comprises determining the volume of plasma in the subject's circulation according to the aforementioned method. The subject invention further provides an apparatus for determining the volume of plasma in a subject's circulation.

27 Claims, 2 Drawing Sheets

METHOD FOR DETERMINING PLASMA VOLUME, DETERMINATION OF BLOOD VOLUME THEREBY, AND APPARATUS THEREFORE

BACKGROUND OF THE INVENTION

Throughout this application various publications are referenced by arabic numerals within parentheses. Full citations for these publications may be found at the end of this application, preceding the claims. The disclosures of these publications in their entireties are hereby incorporated by reference into this application in order to more fully describe the state of the art to which this invention pertains.

Current scientific literature reveals that inflammatory mediators initiate a biochemical chain of events that increase capillary permeability. Under such circumstances the separation of capillary endothelial junctions into gaps cannot keep infused colloids such as serum albumin, Dextran-40, and particular intracapillary fluids within the vessel.

Colloids such as serum albumin escape into the interstitium creating a nonfunctional "third space", the volume of which increases as albumin leakage increases. This leakage widens capillary-cellular distances, creating problems of poor diffusion and transport between the circulatory system and the functional cells and the capillaries, and less oxygen and energy substrates are able to enter the cell and the less carbon dioxide and its acid by-products are able to leave. These events result in cellular anoxia, a cellular energy deficit, acidosis, and possibly sequential organ failure.

In the past, others have approached the problem of albumin leakage and the concurrent creation of a third space through chemical or pharmacological means. U.S. Pat. No. 4,994,444, Zikria, issued Feb. 19, 1991, which is hereby incorporated in its entirety by reference into the subject application, describes a method to solve the problem which involves using natural or synthetic macromolecules as sealants to inhibit the escape of albumin and other macromolecules. These macromolecules are effective because their configuration prohibits their escape through the enlarged capillary endothelial junctions, i.e. the endothelial gaps.

The above-described phenomenon of increased capillary permeability has been termed "capillary leak". Capillary leakage, which results from certain inflammatory mediators, occurs primarily in the 10 to 50 micrometer-diameter post-capillary (pericytic) venules. The mechanism of this leakage was demonstrated almost two decades ago for histamine, serotonin, and bradykinin by electron microscopic studies, which were confirmed in vivo.(1, 2) The endothelial cells in the postcapillary venules have been shown to contract and pull away from each other (3), producing endothelial cell gaps, i.e. endothelial gaps. These endothelial gaps vary from organ to organ, with the tight blood-brain barrier interface constituting one end of the spectrum and the sinusoids of liver the other. It is the modification of these cell junctions following insult that allows the escape of albumin and certain globulins, serum's most important hydrophilic macromolecules, into the interstitium. The entry of albumin with 200 ionic charges and a net charge of −18 (4), and other protein macromolecules into the narrow interstitium, turns this compartment into a nonfunctioning space, the "third space."(5) Problems of oxygen and energy substrate diffusion into cells and clearance of carbon dioxide and other waste products from cells may be the harmful consequences. The resulting interstitial and cellular swelling increases tissue pressures until the lymphatic draining system of the interstitium is collapsed. Ensuing congestion may result in venous and arteriolar occlusion and ischemic necrosis.

Accurately determining blood volume in a subject who has suffered trauma has proven to be difficult. Moreover, current methods for blood volume determination are invasive and impractical.

In the 1960's and 1970's, $I^{125}$ serum albumin was used for blood volume determinations. During that time, "Volumetrons", was used for automated blood volume determinations in a number of major hospital wards. However by 1973, it was recognized that iodinated $I^{125}$ serum albumin had a limited use. An article published in Archives of Medicine in 1973 (6) was one of the best examples of this realization. Valeri et al. confirmed that this method was inaccurate and uniformly over estimated the blood volumes in patients with trauma, cancer, cardiopulmonary disorders and miscellaneous diagnoses.

Plasma volume usually has been measured with iodinated $I^{125}$ serum albumin and red blood cell (RBC) volume by radioactive chromium ($Cr^{51}$) labeled autologous RBC. Having these two measurements, one can calculate the total blood volume. It can also be estimated from either of these measurements and the peripheral venous hematocrit value. Iodinated $I^{125}$ or $I^{131}$ serum albumin is also called radioassay of isotopic iodine-labeled human serum albumin (RIHSA).

The RIHSA measurement of blood volume follows the Fick Principle where concentration of the labeled substance (tracer) is inversely proportional to its volume of dilution; the latter being calculated by the dilution formula of $C1/V1 = C2/V2$ or $C1V2 = C2V1$, wherein C1 and V1 are the concentration and volume of the intravenously injected labeled substance and C2 and V2 are the concentration and volume of the indicator in its volume of distribution within the intravascular space at the time of sampling.

Besides the above blood volume measurement method, since the advent of the Swan-Ganz catheter, indirect measurements of blood volume can be made by thermal dilution technic. This method has proven not to be very accurate in critically ill patients. (7)

Both direct RIHSA and other indirect methods are not very accurate in sick patients. For instance, Valeri et al. in a study of blood volume determinations by RIHSA in 564 patients found this method to over-estimate the plasma volume. However, they found the cold agglutinin labeled with radioactive iodine ($I^{125}$) gave an accurate measurement of plasma volume in 47 comparable patients. They concluded "These data demonstrate the limitations of iodinated albumin molecules in measuring plasma volume and in indirectly estimating RBC volume form the total body hematocrit value and the plasma volume as determined with iodinated $I^{125}$ serum albumin. The best method was by determining red blood cell volume with radioactive chromium (Cr-51) labeled RBC, and estimating plasma volume." (6)

However, RIHSA because of its inaccuracy, and $Cr^{51}$ labeled RBC because it requires numerous steps, and is therefore cumbersome and impractical, have been by and large abandoned. (8) Most recently, Dr. William C. Shoemaker, an authority in the study of shock patients, stated "restoration of blood volume is the most important correctable therapeutic problem in acute circulatory shock . . . it is, therefore, essential to have a reliable means to assess this volume . . . measurements of plasma volume by $I^{125}$ labeled albumin or red cell mass by $Cr^{55}$ or $Cr^{51}$-labeled red blood cells is time consuming, expensive, and usually performed only in research centers." (9)

Following studies of capillary leak, a theory why the $I^{125}$ albumin method is inaccurate and over estimates the blood volume has developed. (10-13) Whenever there is "capillary leak" (14), albumin leaks out of capillaries into interstitial space and equilibrates with a much larger fluid compartment. Tagged RBCs, on the other hand, give accurate blood volume determination because even in leaky capillaries RBCs due to their size and shape rarely leak out of the intravascular space.

The new method of the subject invention for measuring plasma volume rests upon the above facts. Very large macromolecules ("megamolecules", i.e. macromolecules which are larger than about 1,000,000 daltons) such as FITC dextran with an average molecular weight of 2 million daltons (FITC dextran 2000k) are functionally similar to tagged RBCs. Such megamolecules do not leak out of the intravascular space even in subjects with capillary leak, as we have shown in the burn rat model, because of their huge size. FITC dextran 2000k is very stable and degrades very slowly (i.e. over a period of days). These megamolecules, in addition to being as accurate as tagged RBCs for blood volume determination, are practical, not cumbersome, and do not have the disadvantages of radioactivity.

Fluorescein tagged dextran 2000k is harmless and well tolerated in animals. Measurements of very small amounts of fluorescein are now possible by extremely sensitive computerized fluorometers. We have found the Perkin-Elmer SL-30 fluorometer satisfactory in determining very small concentrations of FITC dextran 2000k in plasma for blood volume determinations in rats and hamsters. Technically, it would be simple to build small fluorometers for efficient and accurate bedside measurements of plasma volume and blood volume. Moreover, the method of the subject invention is less invasive and expensive than, and just as accurate as, other existing method for ascertaining blood volume.

SUMMARY OF THE INVENTION

The subject invention provides a method for determining in a subject the volume of plasma in the subject's circulation which comprises: (a) introducing into the subject's circulation a predetermined amount of a pharmaceutically-acceptable solution comprising a predetermined quantity of biodegradable, nontoxic macromolecules, which macromolecules are sufficiently larger than endothelial junctions in the subject's capillaries so that they are incapable of permeating the subject's capillaries, and each of which macromolecules is labeled with a detectable marker; (b) allowing the solution to circulate for a period of time sufficient to distribute the macromolecules throughout the subject's circulatory system; (c) obtaining a sample of plasma from the subject; (d) determining the concentration of macromolecules in the sample by quantitatively measuring the detectable marker in the sample; and (e) calculating the volume of liquid which would dilute the sample to the concentration determined in step (d) from the predetermined amount of solution introduced into the subject's circulation and the predetermined quantity of macromolecules contained therein, thereby determining the volume of plasma in the subject's circulation.

The subject invention also provides a method for determining in a subject the volume of blood in the subject's circulation which comprises determining the volume of plasma in the subject's circulation according to the aforementioned method.

The subject invention further provides an apparatus for determining the volume of plasma in a subject's circulation after introducing into the subject's circulation a predetermined amount of a pharmaceutically-acceptable solution comprising a predetermined quantity of biodegradable, nontoxic macromolecules, which macromolecules are sufficiently larger than endothelial junctions in the subject's capillaries so that they are incapable of permeating the subject's capillaries, and each of which macromolecules is labeled with a detectable marker, which apparatus comprises (a) means for obtaining a sample of plasma from the subject; (b) means for quantitatively measuring the detectable marker in the sample; (c) means for computing the concentration of macromolecules in the sample from the quantity of detectable marker measured by (b); and (d) means for computing the volume of liquid which would dilute the sample to the concentration computed by (c) from the predetermined amount of solution introduced into the subject's circulation and the predetermined quantity of macromolecules contained therein, said volume of liquid being equivalent to the volume of plasma in the subject's circulation.

Blood Volume $V2 =$ $$(\text{Dilution}) \frac{(V_1 FITC\, Dx\, 2000k\, \text{injected}) (\text{Calculated } FITC\, \text{ng/ml})}{FITC\, Dx\, 2000k\, \text{ng/ml}}$$

(1) Dilution Factor $= \dfrac{10{,}000\, \mu L + \text{Plasma Volume in } \mu L}{\text{Plasma Volume in } \mu L}$ Plasma Volume=(length in mm of micro-Ht) $(0.25\, mm^2)$ (2) Standardized flourescence intensity=490 ng/ml (3) FITC Dx 2000k concentration in plasma=(1)×(2)

Results:
Rat experiment above as example:

$$\text{Plasma } V2 = (60) \frac{(1\, ml)\, (80\, ng/ml)}{490\, ng/ml} = 9.8\, ml$$

Figure 2:
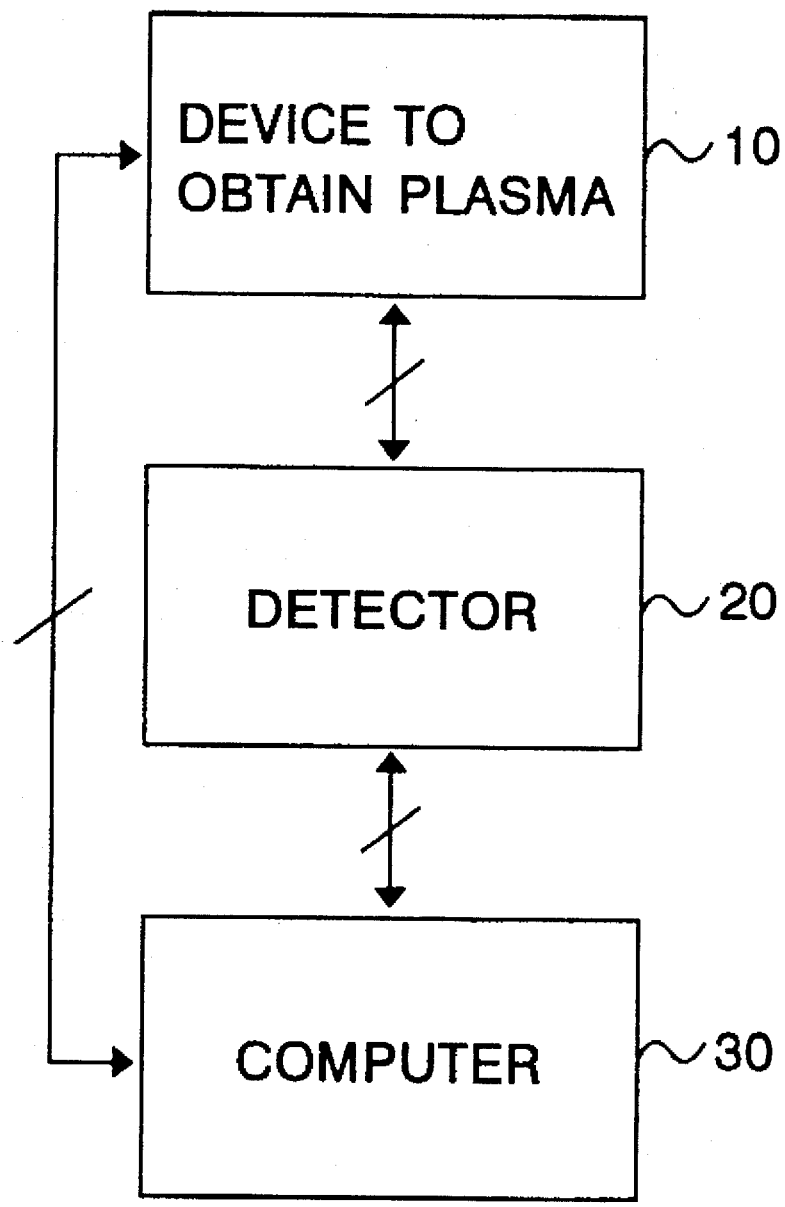

FIG. 2: An embodiment of an apparatus for measuring and displaying plasma volume. FIG. 2 depicts a device for obtaining samples of plasma from a subject (10), a detector to quantify the marker in said sample (20), and a computer to calculate the plasma volume by determining the volume of liquid required to dilute the concentration of marker introduced in the subject to the concentration of marker detected (30).

DETAILED DESCRIPTION OF THE INVENTION

The subject invention provides a method for determining in a subject the volume of plasma in the subject's circulation which comprises (a) introducing into the subject's circulation a predetermined amount of a pharmaceutically-acceptable solution comprising a predetermined quantity of biodegradable, nontoxic macromolecules, which macromolecules are sufficiently larger than endothelial junctions in the subject's capillaries so that they are incapable of permeating the subject's capillaries, and each of which macromolecules is labeled with a detectable marker; (b) allowing the solution to circulate for a period of time sufficient to distribute the macromolecules throughout the subject's circulatory system; (c) obtaining a sample of plasma from the subject; (d) determining the concentration of macromolecules in the sample by quantitatively measuring the detectable marker in the sample; and (e) calculating the volume of liquid which would dilute the sample to the concentration determined in step (d) from the predetermined amount of solution introduced into the subject's circulation and the predetermined quantity of macromolecules contained therein, thereby determining the volume of plasma in the subject's circulation.

Given a solution having a specific predetermined concentration, calculating the volume of liquid necessary to dilute that solution to any particular concentration is well within the skill of the ordinary artist. Using such calculation, one may ascertain the volume of plasma which would dilute the solution of macromolecules introduced into the subject's circulation in the aforementioned method to the concentration determined in step (d), and one may thereby determine the volume of plasma in the subject's circulation. For example, the volume in step (e) may be calculated from the predetermined amount of solution introduced into the subject's circulation and the predetermined quantity of macromolecules contained therein by determining the quantity of macromolecules in the sample from the concentration determined in step (d), dividing the quantity so determined by the quantity of macromolecules in the solution introduced into the subject's circulation, and multiplying the resulting quotient by the amount of solution introduced into the subject's circulation. Alternatively, the volume in step (e) may be calculated by calculating the concentration of macromolecules in the solution introduced into the subject's circulation, dividing the concentration of macromolecules determined in step (d) by the concentration in said solution, and multiplying the resulting quotient by the amount of solution introduced into the subject's circulation.

The above-described method of the subject invention may be used to determine the plasma volume in the circulation of any subject. In one embodiment, the subject is a mammal. In a further embodiment, the subject is a human.

Any method of introducing the solution into the subject's circulation may be used in the method of the subject invention. Methods for introducing a solution into a subject's circulation are well known in the art and include, but are not limited to, introduction by intravenous injection.

For purposes of the subject invention, a pharmaceutically acceptable solution is any solution which is not toxic to the subject into which the solution is injected. Pharmaceutically acceptable solutions useful in the subject method may be formulated using any standard pharmaceutically accepted carrier known to those of ordinary skill in the art. Examples of such standard carriers include, but are not limited to, saline, phosphate buffered saline solution, water, emulsions such as oil/water emulsions or triglyceride emulsions, and various types of wetting agents. A suitable pharmaceutically acceptable carrier may be selected taking into account the mode chosen for introducing the solution into the subject's circulation.

The macromolecules in the above-described method are biodegradable and nontoxic to the subject into which they are introduced, and are incapable of permeating the subject's capillaries. The subject invention is thus advantageous compared to existing methods employing red blood cells, in that the solution used in the method of the subject invention may be easily prepared or obtained, whereas red blood cells used in other existing methods must be obtained from the subject, labeled and reinjected.

Macromolecules suitable for purposes of the subject invention because they are incapable of permeating a subject's capillaries may be readily determined using techniques known to those of ordinary skill in the art. The selection of the particular macromolecule to be used will depend on factors such as the particular subject whose plasma volume is to be determined, the estimated size of endothelial junctions in the subject's capillaries, the size of the macromolecule, and the shape of the macromolecule.

The width of the narrowest of human capillaries is approximately 4–5 microns. Accordingly, the macromolecule used in the subject invention should have a size and shape permitting it to pass through a space as small as 4 to 5 microns. A macromolecule no larger than about 1 micron in width would assure that the molecule would be able to pass through a human subject's smallest capillaries.

The macromolecule selected for use in the subject method should not however be so small as to pass through the endothelial junctions, or "endothelial gaps" as the case may be, of the subject. In a human, healthy capillaries have endothelial junctions of two sizes, the smaller ranging from about 3 to about 6 nanometers in radius, and the larger ranging from about 30 to about 100 nanometers in radius. Thus, if a human subject is expected to have normal capillaries, the selected macromolecule should have a size and shape rendering it incapable of passing through a pore of about 100 nanometers in radius.

The macromolecule used in the subject invention may have any shape, including, but not limited to, a "needle-like" shape, a fibrous shape, or a globular shape. In one embodiment, the macromolecule is a polymer. In different embodiments when the macromolecule is a globular polymer, the macromolecule is derived from hydroxyethyl starch, glycogen, dextran, and hemoglobin. Polymers derived from such molecules are well known and readily available to those of ordinary skill in the art. Hydroxyethyl starch polymers of various weights may, for example, be obtained from Sigma Chemical Company (St. Louis, Mo.).

In the above-described method of the subject invention, any detectable marker may be used to label the macromolecules in the solution introduced into the subject's circulation. Detectable markers are well known in the art. The particular detectable marker selected for use will depend on factors known to those of ordinary skill in the art, including, but not limited to, the toxicity of the marker to the particular subject, and the expense and ease by which the marker may be detected in the subject. Examples of detectable markers which may be used in the method of the subject invention include, but are not limited to fluorophores, such as fluorescein isothiocyanate (FITC); chromophores; and radioactive substances, such as radioactive iodine or chromium.

For purposes of the subject invention, any predetermined quantity of macromolecules may be introduced into the subject's circulation in step (a). In general, the predetermined quantity is preferably the smallest detectable quantity of macromolecule labeled with detectable marker so as to minimize the possibility of toxicity to the subject from the macromolecule and/or the detectable marker.

Any predetermined amount of solution may be introduced into the subject in the method of the subject invention. The predetermined amount will be chosen based on factors known to those of ordinary skill in the art, including, but not limited to, the size of the subject and the mode of introduction.

In the method of the subject invention, after introducing the solution into the subject's circulation, the solution is permitted to circulate for a period of time to distribute the macromolecules therein throughout the subject's circulatory system. A suitable period of time may be determined based on factors well known in the art, including, but not limited to, the size of the subject. If the subject is a human, for example, a sufficient period of time in step (b) is from about 15 to about 20 minutes.

In one embodiment of the method of the subject invention, the subject is predisposed to capillary leak. Conditions predisposing a subject to capillary leak are well known. For example, a subject who has suffered trauma and/or anoxia is predisposed to capillary leak. As used herein, trauma indicates any bodily injury resulting from some external condition or conditions. Examples of trauma which predispose a subject to capillary leak include burns, shock, ischemia, organ transplantation, complications from a surgical technique or techniques, sepsis, poisoning, or anaphylaxis (an allergic reaction). For example, sepsis is associated with "Toxic Shock Syndrome". Thus, a subject suffering "Toxic Shock Syndrome" would be predisposed to capillary leak. As another example, certain poisonings, such as an overdose of salicylic medications, or poisoning by rattle snake venom, are known to result in severe capillary leak. Thus, subjects so poisoned would be predisposed to capillary leak. As a further example, cardiopulmonary bypass surgery is known to cause severe capillary leak in children. Thus, a child who has undergone a cardiopulmonary bypass would be predisposed to capillary leak. The subject invention is particularly useful for subjects predisposed to capillary leak, since the number of existing methods for determining plasma and blood volume for such subjects is even more limited.

Also, certain other conditions, such as Hyaline Membrane Disease and Systemic Capillary Leak Syndrome (a familial condition), are known to predispose a subject to capillary leak. Accordingly, in one embodiment of the method of the subject invention, the subject is possesses a genetic condition predisposing the subject to capillary leak.

Moreover, adverse side effects of certain therapies are known to predispose a subject to capillary leak. Accordingly, in another embodiment of the method of the subject invention, the subject has undergone a therapy predisposing the subject to capillary leak. One therapy which predisposes a subject to capillary leak is immune therapy, such as by treatment with interleukin-2 or treatment with lymphokine activated killer cells (LAK). Immune therapy is useful, for example, for treating cancer in a subject. Another therapy which predisposes a subject to capillary leak is chemotherapy and/or bone marrow transplant. Other therapies which predispose subjects to capillary leak are known to those of ordinary skill in the art.

In the method of the subject invention, if the subject is predisposed to capillary leak, the macromolecules should be of sufficient size and shape so as to be incapable of passing through the enlarged capillary endothelial junctions, i.e. the "capillary endothelial gaps", of the subject. If the macromolecules are globular in shape, a molecular weight greater than or equal to about 1,000,000 daltons is sufficiently large not to pass through the capillary endothelial gaps. If the macromolecules are globular polymers, their average molecular weight should therefore be greater than or equal to about 1,000,000 daltons. As defined above, macromolecules greater than about 1,000,000 daltons are "megamolecules". In one embodiment wherein the macromolecules are globular polymers, their average molecular weight is from about 1,000,000 daltons to about 12,000,000 daltons. In another embodiment wherein the macromolecules are globular in shape, their average molecular weight is from about 1,000,000 to about 6,000,000 daltons. In a further embodiment, the average molecular weight of the macromolecules is from about 1,000,000 daltons to about 2,000,000 daltons.

Globular polymers useful in the aforementioned embodiment of the subject invention wherein the subject is predisposed to shock are well known to those of ordinary skill in the art, and include but are not limited to, derivatives of suitable average molecular weight of hydroxyethyl starch, glycogen, dextran, or hemoglobin. In a further embodiment, wherein the macromolecules labeled with the detectable marker comprise FITC dextran 2000k (Sigma Chemical Company; St. Louis, Mo.), which is a polymer of dextran having an average molecular weight of 2,000,000 daltons labeled with fluorescein isothiocyanate.

The subject invention also provides a method for determining in a subject the volume of blood in the subject's circulation which comprises determining the volume of plasma in the subject's circulation according to the above-described method of the subject invention. The volume of blood may be determined from the volume of plasma obtained according to the subject invention according to any technique or calculation for determining blood volume from plasma volume. Such techniques are well known to those of ordinary skill in the art. For example, blood volume may be determined by multiplying plasma volume by the subject's hematocrit, the hematocrit being the ratio of the volume occupied by the red blood cells in subject's blood to the subject's total blood volume. For any subject, the hematocrit may, for example, be obtained from tables setting forth expected hematocrit values for different subjects, or directly by analyzing a sample of the subject's blood. The hematocrit value obtained for any sample is somewhat affected by the location from which the sample is obtained. Accordingly, the hematocrit obtained for such a sample may be further adjusted by a known factor to obtain the average hematocrit for the subject. For example, if the sample is obtained from a large artery or vein, the sample should be multiplied by (100/(100−0.87).

Accordingly, this invention also provides a method for determining in a subject the volume of blood in the subject's circulation which comprises determining the volume of plasma in the subject's circulation according to the above-described method and multiplying the volume of plasma so determined by the subject's hematocrit. In one embodiment, the subject's hematocrit is ascertained by obtaining a sample of blood from the subject, measuring the volume of the sample, separating erythrocytes from the sample, measuring the volume occupied by the erythrocytes so separated, and calculating the ratio of the volume occupied by the separated erythrocytes to the volume of the sample, the ratio so calculated being equivalent to the subject's hematocrit. Although any method for separating erythrocytes from the sample may be used, in a further embodiment, separating erythrocytes from the sample comprises centrifuging the sample.

The subject invention also provides an apparatus for determining the volume of plasma in a subject's circulation after introducing into the subject's circulation a predetermined amount of a pharmaceutically-acceptable solution comprising a predetermined quantity of biodegradable, non-toxic macromolecules, which macromolecules are sufficiently larger than endothelial junctions in the subject's capillaries so that they are incapable of permeating the subject's capillaries, and each of which macromolecules is labeled with a detectable marker, which apparatus comprises (a) means for obtaining a sample of plasma from the subject; (b) means for quantitatively measuring the detectable marker in the sample; (c) means for computing the concentration of macromolecules in the sample from the quantity of detectable marker measured by (b); and (d) means for computing the volume of liquid which would dilute the sample to the concentration computed by (c) from the predetermined amount of solution introduced into the subject's circulation and the predetermined quantity of macromolecules contained therein, said volume of liquid being equivalent to the volume of plasma in the subject's circulation.

Any means for obtaining a sample from a subject may be used in the apparatus of the subject invention, and such means are well-known in the art. The means for quantitatively measuring the detectable marker in the apparatus of the subject invention will be selected based on the particular detectable marker used. For example, if the detectable marker is a fluorophore, the means for quantitatively measuring the marker may be a fluorometer. Means (c) and (d) of the subject apparatus may comprise a computer and appropriate software for computation. Moreover, the apparatus of the subject invention, may be advantageously designed for bedside use.

The apparatus of the subject invention may further comprise a means for determining the subject's hematocrit, and a means for computing the volume of blood in the subject's circulation from the volume computed by (d) and the hematocrit determined by said means. In one embodiment, the means for determining the subject's hematocrit comprises a means for measuring the subject's hematocrit from the sample obtained by (a).

This invention will be better understood from the Examples in the "Experimental Details" Section which follows. However, one skilled in the art will readily appreciate that the specific methods and results discussed are merely illustrative of, and are not intended to, nor should they be construed to, limit the invention as described more fully in the claims which follow thereafter.

EXPERIMENTAL DETAILS

Protocol for Treatment of Irreversible Hemorrhagic Shock and Determination of Capillary Leak and the Blood Volume Introduction Following severe hemorrhagic shock in Wigger's model, even after total replacement of shed blood plus 10% crystalloids or colloids, death becomes inevitable. This phenomenon, initially reproduced in dogs and more recently in rats, is called "Irreversible Shock". This state of irreversibility is very similar to that seen in critically ill patients in ICU units. This irreversibility initially appears to be related to the development of a generalized "capillary leak", which may also be called "Clinical Capillary Leak Syndrome", in patients. Since it has been able to show that hydroxyethyl starch macromolecules (HES-Pz) diminish the capillary leakage following ischemia-reperfusion injury in isolated organs of rats, dogs, and hamsters, the systemic capillary leakage in the hemorrhagic shock model may also be significantly reduced by HES-Pz. Therefore, it may be possible to reverse the so called "irreversible shock".

Materials and Methods

Sprague-Dawley rats (Average weight-350 g) under sodium pentobarbital (50 mg/Kg) underwent femoral arterial catheterization with a 3-way stopcock polypropylene (PE-50, 0.58 mm ID). MAP was monitored with Millar transducers. Blood was drawn by heparinized syringes to bring MAP to 30–40 mm Hg. Upto 90 minutes, the MAP was maintained at these pressures by infusing or withdrawing the necessary amount of blood. At 90 minutes shock period, animals were resuscitated with their own shed blood, which produces about 40–50% mortality in 24 hours. The following groups were be compared for a) 24 hr. mortality, b) total body weight, c) organ weights and organ potassium an water content (lungs, liver, heart, kidneys and small bowel):

Group I: sham;

Group II: resuscitated with shed blood;

Group III: resuscitated with four times volume of shed blood as Ringer's lactate;

Group IV: resuscitated with shed blood+10% of shed blood as Ringer's lactate;

Group V: resuscitated with shed blood+10% of shed blood as 12% Albumin;

Group VI: resuscitated with shed blood+10% of shed blood as 12% Hespan;

Group VII: resuscitated with shed blood+10% of shed blood as 12% HES-Pz.

In addition, pre-shock and post-shock plasma volumes were measured according to the technique of the subject invention by intravenous use of FITC dextran 2000k for more accurate determinations, since these molecules do not leak out of leaky capillaries as radioactive albumin molecules do.

Results

Figure 1:
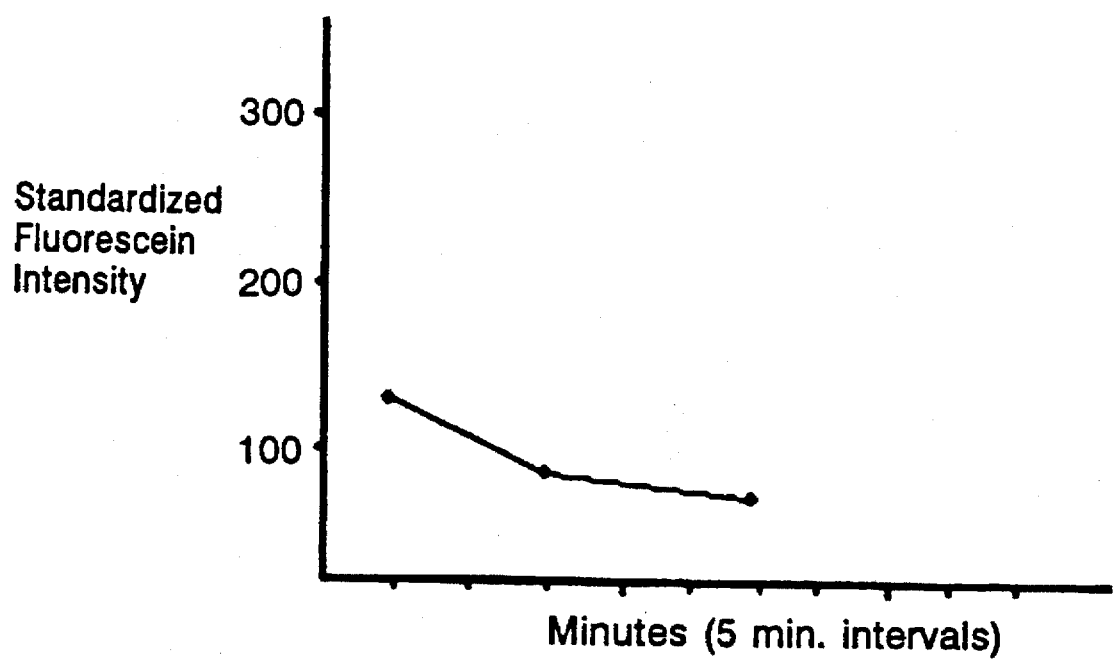
FIG. 1: Calculating blood volume determination according to the subject method using FITC dextran 2000k (FITC Dx 2000k). The sample was drawn from a rat suffering from so called "irreversible shock" as in Wigger's model after allowing an FITC dextran 2000k solution to circulate in the rat's circulation for approximately thirty minutes. The fluorescein isothiocyanate (FITC) concentration in the sample was measured by comparing the fluorescein isothiocyanate intensity of the sample to the intensity of a standardized solution. The dilution factor adjusts the calculation to account for the volume of distilled water added to the sample drawn from the rat in order to achieve a volume which may be measured in the fluorometer.

FIG. 1 illustrates calculating blood volume determination according to the subject method using FITC dextran 2000k (FITC Dx 2000k). The sample was drawn from the treated rats after allowing the FITC dextran 2000k solution to circulate in the rats' circulation for approximately thirty minutes. The fluorescein isothiocyanate (FITC) concentration in the sample was measured by comparing the fluorescein isothiocyanate intensity of the sample to the intensity of a standardized solution.

REFERENCES

1. Arturson G. Microvascular permeability to macromolecules in thermal injury. Acta Physiol Scand. 1979;463:111–122.

2. Joris I. Majno G. Corey E J, Levis R A. The mechanism of vascular leakage induced by leukotriene E4: endothelial contraction. Ann Pathol. 1987;126:19–24.

3. Majno G. Shea S M, Leventhal M. Endothelial contraction induced by histamine-type medistors; an electroa microscopic study. J Cell Biol. 1969;42:647–672.

4. Peters Jr T. Serum albumin; adventures of circulating proteins. In:Schecter A. N. Dean A, Goldberg R F, eds. The Impact of Protein chemistry on Biological Sciences. Orlando, Fla: Academic Press Inc; 1984;39–55.

5. Gann D S, Amaral J F, Caldwell M D. Metabolic response to injury, stress, and starvation. In: Drucker W R, Gann D S, Foster R S, Gamelli R L, Pruitt B A, Sheldon G F, eds. Clinical Surgery, St Louis, Mo;CV Mosby Co: 1987;367–368

6. Valeri C R, Cooper A C, Pivacek L E. Limitations of Measuring Blood Volume with Iodinated I-125 Serum Albumin. Arch Int Med 1973; 132:534

7. Shoemaker W C. Pathophysiology and Fluid Management of Postoperative and Posttraumatic ARDS. Assessment of Blood Volume Deficit. In: Shoemaker W C, Ayers S, Grenvick A, et al. eds. Textbook of Critical Care. Philadelphia: Saunders 1989:626

8. Shippy C R, Appel P L, Shoemaker W C. Reliability of clinical monitoring to asses blood volume in critically ill patients. Crit Care Med 1984; 12:

9. Shoemaker W C. Shock syndromes as Reperfusion Injuries: Pathophysiology, hemodynamic and oxygen transport patterns, outcome predictions, and therapy. In: Zikria B A, Oz M C, Carlson R W, eds.Reperfusion injuries and Clinical Capillary Leak syndromes. New York: Futura Publishing Co. Inc. 1994

10. Zikria B A, Stanford J, Freeman H P, King T C. A Biophysical Approach to Capillary permeability. surgery 1989:105:625

11. Zikria B A, SubbaRao C, Oz M C, et al. Sealing of Capillary Leak in Rat Limb Ischemia-reperfusion Injury. Crit Care Med 1989; 17:1306

12. Zikria B A, SubbaRao C, Oz M C, et al. Hudoxyethyl Starch macromolecules reduce Myocardial Reperfusion Injury. Arch Surg 1990; 125:930

13. Oz M C, Zikria B A, McLeod P F. Hydroxyethyl Starch Macromolecules and Superoxide Dismutase Effects on Myocardial Reperfusion Injury. Amer J Surgery 1991; 162:59

14. Taylor A E, Parker J C, Allison R C, et al. Capillary exchange of fluid and Protein. Leaky Capillary Syndromes. In: Shoemaker W C, Ayers S, Grenvick A, et al., eds Text book of Critical Care. Philadelphia: W B Saunders 1989:1044

What is claimed is:

1. A method for determining in a subject the volume of plasma in the subject's circulation which comprises:
   (a) introducing into the subject's circulation a predetermined amount of a pharmaceutically-acceptable solution comprising a predetermined quantity of biodegradable, nontoxic macromolecules, which macromolecules are sufficiently larger than endothelial junctions in the subject's capillaries so that they are incapable of permeating the subject's capillaries, and each of which macromolecules is labeled with a detectable marker;
   (b) allowing the solution to circulate for a period of time sufficient to distribute the macromolecules throughout the subject's circulatory system;
   (c) obtaining a sample of plasma from the subject;
   (d) determining the concentration of macromolecules in the sample by quantitatively measuring the detectable marker in the sample; and
   (e) calculating the volume of liquid which would dilute the sample to the concentration determined in step (d) from the predetermined amount of solution introduced into the subject's circulation and the predetermined quantity of macromolecules contained therein, thereby determining the volume of plasma in the subject's circulation.

2. The method of claim 1, wherein the volume in step (e) is calculated by determining the quantity of macromolecules in the sample from the concentration determined in step (d), dividing the quantity so determined by the quantity of macromolecules in the solution introduced into the subject's circulation, and multiplying the resulting quotient by the amount of solution introduced into the subject's circulation.

3. The method of claim 1, wherein the volume in step (e) is calculated by calculating the concentration of macromolecules in the solution introduced into the subject's circulation, dividing the concentration of macromolecules determined in step (d) by the concentration in said solution, and multiplying the resulting quotient by the amount of solution introduced into the subject's circulation.

4. The method of claim 1, wherein the subject is a mammal.

5. The method of claim 4, wherein the subject is a human.

6. The method of claim 1, wherein the solution is introduced into the subject's circulation by intravenous injection.

7. The method of claim 1, wherein the macromolecules are derived from hydroxyethyl starch.

8. The method of claim 1, wherein the macromolecules are derived from glycogen.

9. The method of claim 1, wherein the macromolecules are derived from dextran.

10. The method of claim 1, wherein the macromolecules are derived from hemoglobin.

11. The method of claim 1, wherein the detectable marker is a fluorophore, a chromophore, or a radioactive substance.

12. The method of claim 1, wherein the period of time in step (b) is from about 15 to about 20 minutes.

13. The method of claim 12, wherein the macromolecules are globular in shape.

14. The method of claim 13, wherein the macromolecules have an average molecular weight greater than or equal to about 1,000,000 daltons.

15. The method of claim 14, wherein the macromolecules have an average molecular weight of from about 1,000,000 daltons to about 12,000,000 daltons.

16. The method of claim 14, wherein the macromolecules are derived from hydroxyethyl starch.

17. The method of claim 14, wherein the macromolecules are derived from glycogen.

18. The method of claim 14, wherein the macromolecules are derived from dextran.

19. The method of claim 14, wherein the macromolecules are derived from hemoglobin.

20. The method of claim 19, wherein the macromolecules comprise FITC dextran 2000k.

21. A method for determining in a subject the volume of blood in the subject's circulation which comprises determining the volume of plasma in the subject's circulation according to the method of claim 1 and calculating the volume of blood from the volume of plasma.

22. A method for determining in a subject the volume of blood in the subject's circulation which comprises determining the volume of plasma in the subject's circulation according to the method of claim 1 and multiplying the volume of plasma so determined by the subject's hematocrit.

23. The method of claim 22, further comprising ascertaining the subject's hematocrit by obtaining a sample of blood from the subject, measuring the volume of the sample, separating erythrocytes from the sample, measuring the volume occupied by the erythrocytes so separated, and calculating the ratio of the volume occupied by the separated erythrocytes to the volume of the sample, the ratio so calculated being equivalent to the subject's hematocrit.

24. The method of claim 23, wherein separating erythrocytes from the sample comprises centrifuging the sample.

25. An apparatus for determining the volume of plasma in a subject's circulation after introducing into the subject's circulation a predetermined amount of a pharmaceutically-acceptable solution comprising a predetermined quantity of biodegradable, nontoxic macromolecules, which macromolecules are sufficiently larger than endothelial junctions in the subject's capillaries so that they are incapable of permeating the subject's capillaries, and each of which macromolecules is labeled with a detectable marker, which apparatus comprises:

(a) means for obtaining a sample of plasma from the subject;

(b) means for quantitatively measuring the detectable marker in the sample;

(c) means for computing the concentration of macromolecules in the sample from the quantity of detectable marker measured by (b); and (d) means for computing the volume of liquid which would dilute the sample to the concentration computed by (c) from the predetermined amount of solution introduced into the subject's circulation and the predetermined quantity of macromolecules contained therein, said volume of liquid being equivalent to the volume of plasma in the subject's circulation.

26. The apparatus of claim 25, further comprising a means for determining the subject's hematocrit, and a means for computing the volume of blood in the subject's circulation from the volume computed by (d) and the hematocrit determined by said means.

27. The apparatus of claim 26, wherein said means for determining the subject's hematocrit comprises a means for measuring the subject's hematocrit from the sample obtained by (a).

* * * * *